(12) United States Patent
Kanazawa

(10) Patent No.: US 9,126,021 B2
(45) Date of Patent: Sep. 8, 2015

(54) GUIDEWIRE

(71) Applicant: ASAHI INTECC CO., LTD., Nagoya-shi, Aichi (JP)

(72) Inventor: Yuuya Kanazawa, Seto (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 158 days.

(21) Appl. No.: 13/926,650

(22) Filed: Jun. 25, 2013

(65) Prior Publication Data

US 2014/0031719 A1 Jan. 30, 2014

(30) Foreign Application Priority Data

Jul. 27, 2012 (JP) ................................. 2012-166451

(51) Int. Cl.
*A61M 25/00* (2006.01)
*A61M 25/09* (2006.01)

(52) U.S. Cl.
CPC ..... *A61M 25/09* (2013.01); *A61M 2025/09083* (2013.01); *A61M 2025/09175* (2013.01)

(58) Field of Classification Search
CPC ................. A61M 2025/09083; A61M 25/09; A61M 2025/09175; A61M 2025/09166; A61M 25/0113; A61M 25/0108
USPC ....................... 600/433, 434, 585; 604/164.13
See application file for complete search history.

(56) References Cited

U.S. PATENT DOCUMENTS

| 6,620,114 B2 * | 9/2003 | Vrba et al. ................. 600/585 |
| 2002/0198468 A1 | 12/2002 | Kato et al. |
| 2004/0122340 A1 | 6/2004 | Vrba et al. |
| 2007/0282225 A1 * | 12/2007 | Terashi et al. ............. 600/585 |

FOREIGN PATENT DOCUMENTS

| EP | 0 611 073 A1 | 8/1994 |
| EP | 2 263 735 A1 | 12/2010 |
| EP | 2 361 652 A1 | 8/2011 |
| JP | A-H06-178811 | 6/1994 |
| JP | A-H6-292729 | 10/1994 |
| JP | A-2001-178829 | 7/2001 |
| WO | WO 98/18516 A1 | 5/1998 |

OTHER PUBLICATIONS

Nov. 14, 2013 European Search Report issued in European Patent Application No. EP 13172988.1.

* cited by examiner

*Primary Examiner* — Max Hindenburg
*Assistant Examiner* — Jonathan M Foreman
(74) *Attorney, Agent, or Firm* — Oliff PLC

(57) ABSTRACT

A guidewire includes a first junction that joins a distal end of an inner coil body and a portion of a core shaft positioned a non-zero distance away from a distal end toward a proximal end; a second junction that joins a proximal end of the inner coil body and the core shaft; a third junction that joins a distal end of the outer coil body and the distal end of the core shaft; and a fourth junction that joins a proximal end of the outer coil body and the core shaft. The outer coil body includes a tapered coil portion and a uniform-diameter coil portion. The inner coil body is disposed inside the uniform-diameter coil portion of the outer coil body. The inner coil body is joined to the core shaft at only the first and second junctions but is not joined to the outer coil body.

14 Claims, 4 Drawing Sheets

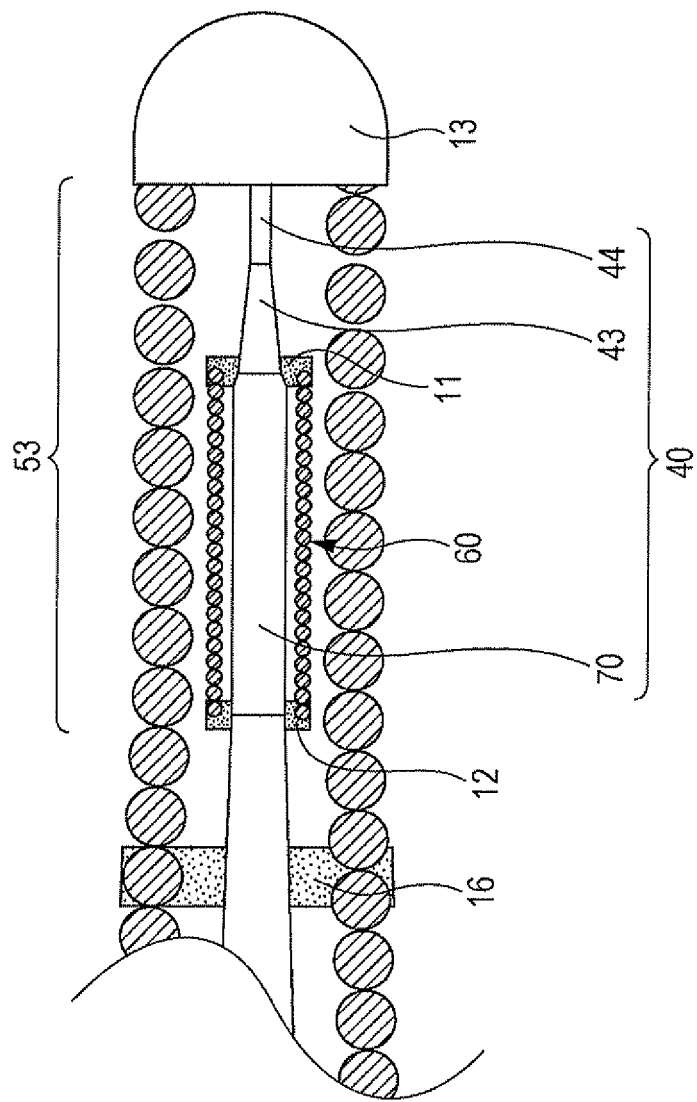

GUIDEWIRE

CROSS-REFERENCE TO RELATED APPLICATION

The present application claims priority to Japanese Patent Application No. 2012-166451 filed in the Japan Patent Office on Jul. 27, 2012, the entirety of which is hereby incorporated by reference.

BACKGROUND

1. Field

The disclosed embodiments relate to a medical device. Specifically, the disclosed embodiments relate to guidewires for medical use.

2. Description of Related Art

Various types of guidewires have been developed for performing treatment or inspection. The guidewires guide a catheter or other devices inserted into a tubular organ, such as a blood vessel, an alimentary canal, a ureter, or internal bodily tissue.

For example, Japanese Unexamined Patent Application Publication No. H6-292729 discloses a guidewire in which a distal end portion of a core shaft is covered by two coil bodies, one of which is overlapped by the other. In addition, Japanese Unexamined Patent Application Publication No. 2001-178829 discloses a guidewire having a distal end portion that is tapered such that its diameter decreases toward the distal end.

SUMMARY

If, however, an outer one of the two coil bodies of the guidewire covering the distal end portion of the core shaft is tapered, the outer coil body is more likely to interfere with the inner coil body at the smaller diameter side (distal end side). If the outer coil body interferes with the inner coil body, the distal end portion becomes less flexible and bends less easily. Thus, the distal end portion becomes less capable of exactly following a complex tubular path.

The disclosed embodiments have been developed in view of the above-described circumstances and aim to provide a guidewire that is capable of exactly following a complex, winding, tubular path when passing through the path.

To provide such a guidewire, a guidewire according to one embodiment is configured in the following manner.

A guidewire according to one embodiment includes a core shaft; an outer coil body that covers an outer periphery of the core shaft; an inner coil body that is disposed on an inner side of the outer coil body and that covers a distal end portion of the core shaft; a first junction that joins together a distal end of the inner coil body and a portion of the core shaft positioned at a non-zero distance from a distal end of the core shaft toward a proximal end of the core shaft; a second junction that joins a proximal end of the inner coil body and the core shaft together; a third junction that joins a distal end of the outer coil body and the distal end of the core shaft together; and a fourth junction that joins a proximal end of the outer coil body and the core shaft together. The outer coil body includes a tapered coil portion and a uniform-diameter coil portion, the tapered coil portion having a diameter that decreases toward the distal end of the outer coil body, the uniform-diameter coil portion being positioned on a distal end side of the tapered coil portion and having a uniform coil outer diameter. The inner coil body is disposed on an inner side of the uniform-diameter coil portion of the outer coil body. The inner coil body is joined to the core shaft at only the first junction and the second junction but not joined to the outer coil body.

In the guidewire according to the above embodiment, a distal end of the inner coil body is joined to the core shaft at a position away from a distal end of the core shaft toward a proximal end of the core shaft. The outer coil body includes a tapered coil portion and a uniform-diameter coil portion, the tapered coil portion having a diameter that decreases toward the distal end of the outer coil body, the uniform-diameter coil portion being positioned on a distal end side of the tapered coil portion and having a uniform coil outer diameter. The inner coil body is disposed on the inner side of the uniform-diameter coil portion of the outer coil body. The inner coil body is joined to the core shaft at only the first junction and the second junction but not joined to the outer coil body. Thus, a tip portion of the guidewire can remain flexible while having a high rigidity due to the presence of the inner coil body. In addition, the inner coil body and the outer coil body can be prevented from interfering with each other while the guidewire remains highly insertable due to the presence of the uniform-diameter coil portion and the tapered coil portion. Consequently, the guidewire is capable of exactly following a complex, winding, tubular path by flexibly bending along the path when passing through the path.

BRIEF DESCRIPTION OF THE DRAWINGS

FIG. 4 illustrates part of a guidewire according to a third embodiment in an enlarged manner.

DETAILED DESCRIPTION

Figure 1:
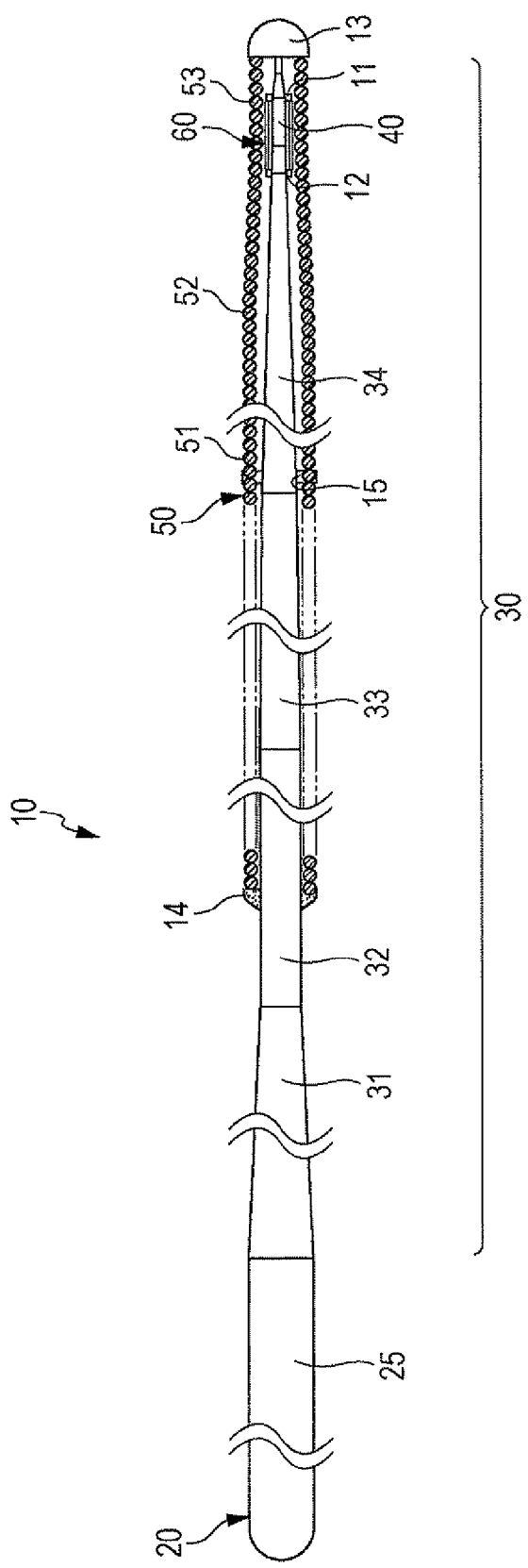
FIG. 1 illustrates the entirety of a guidewire according to a first embodiment.
Figure 2:
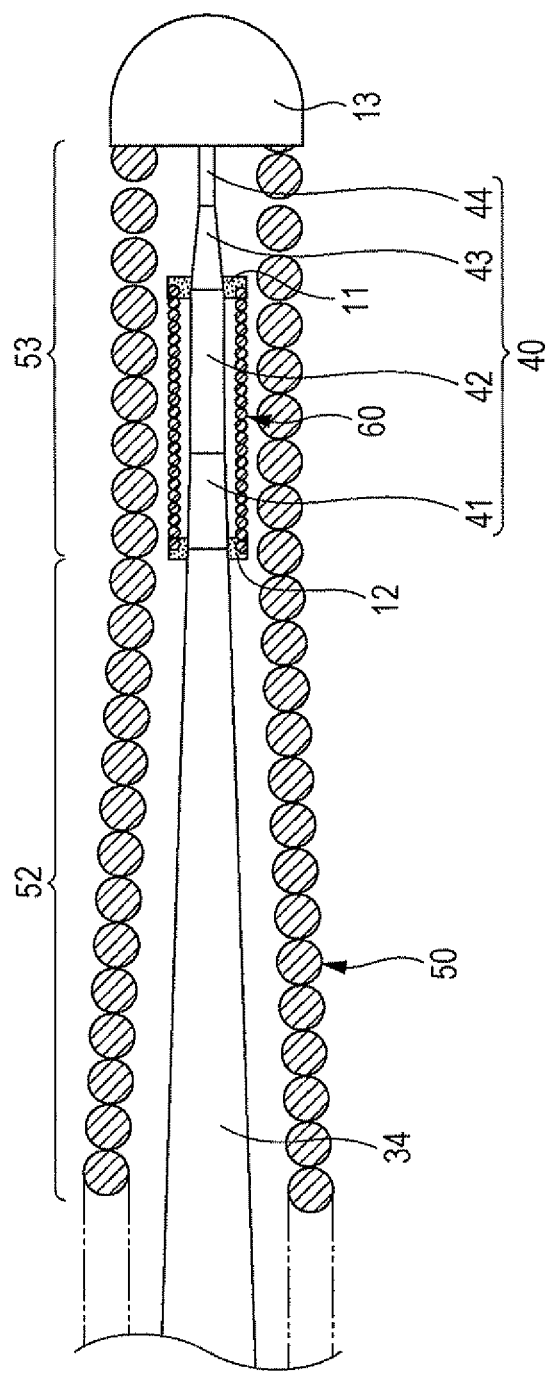
FIG. 2 illustrates part of the guidewire illustrated in FIG. 1 in an enlarged manner.

Referring to FIGS. 1 and 2, a guidewire 10 according to a first embodiment will be described. In FIGS. 1 and 2, the right side is a distal side that is inserted into a body while the left side is a proximal side that is manipulated by a technician such as a doctor.

The guidewire 10 illustrated in FIGS. 1 and 2 is mainly used for a cardiovascular treatment and has a full length of approximately 1,900 mm. The guidewire 10 includes a core shaft 20, an outer coil body 50 that covers the outer periphery of the core shaft 20, and an inner coil body 60 that is disposed on the inner side of the outer coil body 50 and covers a tip portion 40 of the core shaft 20.

The core shaft 20 is roughly divided into a main portion 25 and a distal side portion 30. The main portion 25 is a portion of the core shaft 20 that is the nearest to the proximal end of the guidewire 10 among the portions of the core shaft 20. The main portion 25 has a cylindrical shape having a uniform outer diameter. The distal side portion 30 includes, in order from the proximal end toward the distal end of the guidewire 10: a first tapered portion 31, a uniform-diameter portion 32, a second tapered portion 33, a third tapered portion 34, and a tip portion 40.

The first tapered portion 31 is a tapered portion having a circular cross section. The uniform-diameter portion 32 is a cylindrical portion having a circular cross section and a uniform diameter. The second tapered portion 33 and the third tapered portion 34 are tapered portions having circular cross sections and tapered at different angles. The first tapered portion 31, the uniform-diameter portion 32, the second tapered portion 33, and the third tapered portion 34 may be arranged differently or have different dimensions for purposes such as the purpose of obtaining a desired rigidity. The number of tapered portions and the angles at which the tapered portions are tapered may be appropriately determined as required. The material of the core shaft 20 is not particularly limited although a stainless steel of Japanese Industrial Standards (JIS) No. SUS304 is used in the embodiment. Other examples of the material include superelastic alloys, such as a nickel-titanium (Ni—Ti) alloy, and a piano wire.

As illustrated in FIG. 2, the tip portion 40 includes, in order from the proximal end toward the distal end of the guidewire 10: a first tapered pliable portion 41, a first columnar pliable portion 42, a second tapered pliable portion 43, and a second columnar pliable portion 44. The tip portion 40 is a portion having the least flexural rigidity among all the portions of the core shaft 20. In particular, the second columnar pliable portion 44 has the smallest diameter and the least flexural rigidity among all the portions of the tip portion 40.

Each of the first and second tapered pliable portions 41 and 43 is a tapered portion having a circular cross section and a diameter that decreases toward the distal end. Each of the first and second columnar pliable portions 42 and 44 is a cylindrical portion having a circular cross section and a uniform diameter.

As illustrated in FIG. 1, the outer coil body 50 includes a proximal uniform-diameter coil portion 51, a tapered coil portion 52, and a distal uniform-diameter coil portion 53. A wire that the outer coil body 50 is made of has a uniform outer diameter (wire diameter) throughout the length.

The proximal uniform-diameter coil portion 51 is a proximal portion of the outer coil body 50 and has a uniform coil outer diameter. The proximal end of the proximal uniform-diameter coil portion 51 is brazed to the uniform-diameter portion 32 of the core shaft 20. This brazed portion is a fourth junction 14. A middle portion of the proximal uniform-diameter coil portion 51 is brazed to the third tapered portion 34 of the core shaft 20. This brazed portion is a fifth junction 15.

The tapered coil portion 52 is positioned between the proximal uniform-diameter coil portion 51 and the distal uniform-diameter coil portion 53. The diameter of the tapered coil portion 52 decreases toward the distal end.

The distal uniform-diameter coil portion 53 is a distal portion of the outer coil body 50 and has a uniform coil outer diameter. The distal end of the distal uniform-diameter coil portion 53 is brazed to the distal end of the second columnar pliable portion 44 of the core shaft 20. This brazed portion is a third junction 13.

The inner coil body 60 is disposed on an inner side of the distal uniform-diameter coil portion 53 of the outer coil body 50. A wire that the inner coil body 60 is made of has a uniform outer diameter (wire diameter) throughout the length. The distal end of the inner coil body 60 is brazed to a joint between the first columnar pliable portion 42 and the second tapered pliable portion 43 of the core shaft 20. This brazed portion is a first junction 11. Thus, the distal end of the inner coil body 60 is joined to a portion of the core shaft 20 positioned at a predetermined, non-zero distance from the distal end of the core shaft 20 toward the proximal end. Among the portions of the tip portion 40 of the core shaft 20, the second tapered pliable portion 43 and the second columnar pliable portion 44 are not covered by the inner coil body 60. The proximal end of the inner coil body 60 is brazed to a joint between the third tapered portion 34 and the tip portion 40 (first tapered pliable portion 41) of the core shaft 20. This brazed portion is a second junction 12. The inner coil body 60 is joined to the core shaft 20 at only the first junction 11 and the second junction 12. There is no junction between the inner coil body 60 and the outer coil body 50.

The outer coil body 50 and the inner coil body 60 according to the embodiment may be a single-strand coil including a single wire or a multi-strand coil obtained by twisting multiple wires together. In view of the rigidity or torque transfer capability, however, it is preferable that the outer coil body 50 be a single-strand coil and the inner coil body 60 be a multi-strand coil.

The material of the outer coil body 50 or the inner coil body 60 is not particularly limited although a stainless steel is used in the embodiment. Other examples of the material include superelastic alloys such as a nickel-titanium (Ni—Ti) alloy. Alternatively, wires made of various different materials may be combined together.

In the guidewire 10 having the above configuration, the distal end of the inner coil body 60 is joined to the core shaft 20 at a position away from the distal end of the core shaft 20 toward the proximal end of the core shaft 20. The outer coil body 50 includes a tapered coil portion 52, whose diameter decreases toward its distal end, and a distal uniform-diameter coil portion 53, which is positioned at a position closer to the distal end than the position at which the tapered coil portion 52 is positioned, and has a uniform coil outer diameter. The inner coil body 60 is disposed on the inner side of the distal uniform-diameter coil portion 53 of the outer coil body 50. There is no junction between the inner coil body 60 and the outer coil body 50. The inner coil body 60 is joined to the core shaft 20 at only the first junction 11 and the second junction 12. Thus, the tip portion (the second tapered pliable portion 43 and the second columnar pliable portion 44) can remain flexible while having a high rigidity due to the presence of the inner coil body 60. In addition, the inner coil body 60 and the outer coil body 50 can be prevented from interfering with each other while the guidewire 10 remains highly insertable due to the presence of the distal uniform-diameter coil portion 53 and the tapered coil portion 52. Consequently, the guidewire 10 is capable of exactly following a complex, winding, tubular path by flexibly bending along the path when passing through the path.

Since the guidewire 10 according to the embodiment includes the fifth junction 15 at a position between the second junction 12 and the fourth junction 14, the outer coil body 50 and the inner coil body 60 can be more effectively prevented from interfering with each other even when a distal end portion of the guidewire 10 bends.

Figure 3:
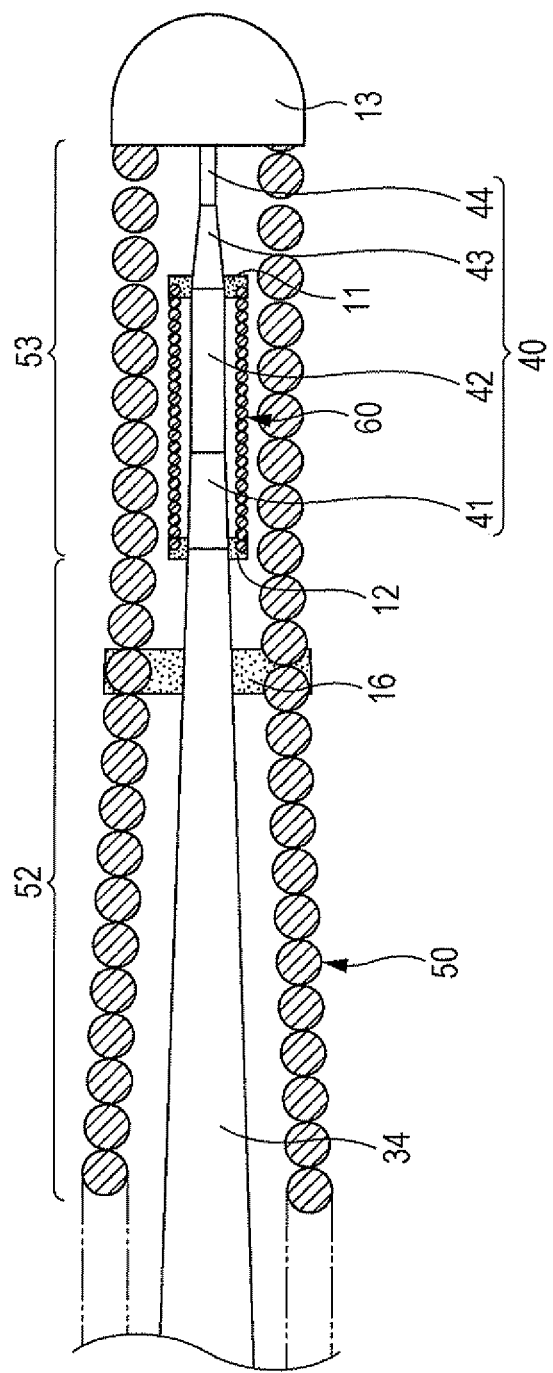
FIG. 3 illustrates part of a guidewire according to a second embodiment in an enlarged manner.

Referring now to FIG. 3, a guidewire according to a second embodiment will be described. In FIG. 3, the right side is a distal side that is inserted into a body while the left side is a proximal side that is manipulated by a technician such as a doctor. Components that are the same as those according to the first embodiment are denoted by the same reference symbols and are not described. Different points are mainly described below.

The guidewire according to the second embodiment differs from the guidewire according to the first embodiment in that a fifth junction 16 is provided at the tapered coil portion 52 of the outer coil body 50.

Since the fifth junction 16 is provided at the tapered coil portion 52 of the outer coil body 50 in the second embodiment, the outer coil body 50 can be joined to the core shaft 20 at a position closer to the distal end than a position at which the fifth junction 15 according to the first embodiment is joined to the core shaft 20. Consequently, a clearance between the outer coil body 50 and the inner coil body 60 can be more reliably secured. Moreover, the outer coil body 50 and the inner coil body 60 can be more effectively prevented from interfering with each other even when the distal end portion bends. Thus, the guidewire is capable of exactly following a complex, winding, tubular path when passing through the path.

The fifth junction 16 according to the second embodiment may be provided in addition to or instead of the fifth junction 15 according to the first embodiment. One or more fifth junctions 16 may be provided.

Referring now to FIG. 4, a guidewire according to a third embodiment will be described. In FIG. 4, the right side is a distal side that is inserted into a body while the left side is a proximal side that is manipulated by a technician such as a doctor. Components that are the same as those according to the first or second embodiment are denoted by the same reference symbols and are not described. Different points are mainly described below.

The guidewire according to the third embodiment differs from the guidewires according to the first and second embodiments in that a portion 70 of the core shaft 20 that is covered by the inner coil body 60 has a uniform outer diameter.

Since the portion 70 of the core shaft 20 covered by the inner coil body 60 has a uniform outer diameter in the third embodiment, not only the clearance between the coil bodies 50 and 60, but also a clearance between the core shaft 20 and the inner coil body 60 can be more reliably secured. Moreover, the core shaft 20, the inner coil body 60, and the outer coil body 50 can be effectively prevented from interfering with one another even when the distal end portion bends. Thus, the guidewire is capable of exactly following a complex, winding, tubular path when passing through the path.

The embodiments described above are provided for illustrative purposes only and are not meant to be limiting. Thus, the disclosed embodiments can be changed and modified in various manners without departing from the invention.

In the above-described embodiments, the guidewire 10 mainly being used for a cardiovascular treatment is described as an example. The above described embodiments are also applicable to a guidewire used, for example, for treatment or inspection of a blood vessel of a body part other than the heart, such as a leg, or an internal organ other than the heart.

What is claimed is:

1. A guidewire comprising:
   a core shaft;
   an outer coil body that covers an outer periphery of the core shaft and includes a tapered coil portion and a uniform-diameter coil portion, the tapered coil portion having a diameter that decreases toward a distal end of the outer coil body, the uniform-diameter coil portion being positioned on a distal end of the tapered coil portion and having a uniform coil outer diameter;
   an inner coil body that is disposed inside the outer coil body and that covers a distal end portion of the core shaft;
   a first junction that joins a distal end of the inner coil body and a portion of the core shaft, the first junction being spaced a non-zero distance from a distal end of the core shaft toward a proximal end of the core shaft;
   a second junction that joins a proximal end of the inner coil body and the core shaft;
   a third junction that joins the distal end of the outer coil body and the distal end of the core shaft;
   a fourth junction that joins a proximal end of the outer coil body and the core shaft; and
   a fifth junction located in the tapered coil portion of the outer coil body and that joins the tapered coil portion of the outer coil body to the core shaft,
   wherein the inner coil body is disposed inside of the uniform-diameter coil portion of the outer coil body, the inner coil body is joined to the core shaft at only the first junction and the second junction, and the inner coil body is not joined to the outer coil body.

2. The guidewire according to claim 1, wherein the distal end portion of the core shaft covered by the inner coil body has a uniform outer diameter.

3. A guidewire comprising:
   an outer coil body that includes a tapered coil portion and a uniform-diameter coil portion, the tapered coil portion having a diameter that decreases toward a distal end of the outer coil body, the uniform-diameter coil portion being positioned on a distal end of the tapered coil portion and having a uniform coil outer diameter;
   a core shaft disposed within the outer coil body and having a distal end portion that includes, from a proximal end of the distal end portion toward a distal end of the distal end portion, a first tapered portion, a first columnar portion, a second tapered portion, and a second columnar portion;
   an inner coil body that is disposed between the uniform-diameter coil portion of the outer coil body and the distal end portion of the core shaft, but that does not cover the second tapered portion of the core shaft or the second columnar portion of the core shaft;
   a first junction that joins a distal end of the inner coil body to the core shaft;
   a second junction that joins a proximal end of the inner coil body to the core shaft;
   a third junction that joins the distal end of the outer coil body to the distal end of the distal end portion of the core shaft; and
   a fourth junction that joins a proximal end of the outer coil body to the core shaft,
   wherein the inner coil body is joined to the core shaft at only the first junction and the second junction, and is not joined to the outer coil body.

4. The guidewire according to claim 3, wherein the outer coil body is further joined to the core shaft at a fifth junction positioned between the second junction and the fourth junction.

5. The guidewire according to claim 4, wherein the fifth junction is located in the tapered coil portion of the outer coil body and joins the tapered coil portion of the outer coil body to the core shaft.

6. The guidewire according to claim 4, wherein the inner coil body covers the first columnar portion of the core shaft.

7. The guidewire according to claim 6, wherein the inner coil body further covers the first tapered portion of the core shaft.

8. The guidewire according to claim 3, wherein the inner coil body covers the first columnar portion of the core shaft.

9. The guidewire according to claim 8, wherein the inner coil body further covers the first tapered portion of the core shaft.

10. The guidewire according to claim 5, wherein the inner coil body covers the first columnar portion of the core shaft.

11. The guidewire according to claim 10, wherein the inner coil body further covers the first tapered portion of the core shaft.

12. A guidewire comprising:
    an outer coil body that includes a tapered coil portion and a uniform-diameter coil portion, the tapered coil portion having a diameter that decreases toward a distal end of the outer coil body, the uniform-diameter coil portion being positioned on a distal end of the tapered coil portion and having a uniform coil outer diameter;
a core shaft disposed within the outer coil body and having a distal end portion that includes, from a proximal end of the distal end portion toward a distal end of the distal end portion, a first tapered portion, a first columnar portion, a second tapered portion, and a second columnar portion;
an inner coil body that is disposed between the uniform-diameter coil portion of the outer coil body and the distal end portion of the core shaft, and that covers only the first tapered portion of the core shaft and the first columnar portion of the core shaft;
a first junction that joins a distal end of the inner coil body to the core shaft;
a second junction that joins a proximal end of the inner coil body to the core shaft;
a third junction that joins the distal end of the outer coil body to the distal end of the distal end portion of the core shaft; and
a fourth junction that joins a proximal end of the outer coil body to the core shaft,
wherein the inner coil body is joined to the core shaft at only the first junction and the second junction, and is not joined to the outer coil body.

13. The guidewire according to claim 12, wherein the outer coil body is further joined to the core shaft at a fifth junction positioned between the second junction and the fourth junction.

14. The guidewire according to claim 13, wherein the fifth junction is located in the tapered coil portion of the outer coil body and joins the tapered coil portion of the outer coil body to the core shaft.

* * * * *